(12) United States Patent
Dewaegenaere

(10) Patent No.: US 10,265,114 B2
(45) Date of Patent: Apr. 23, 2019

(54) SYSTEM AND METHOD FOR CONTROLLING THE OPERATION OF A THERAPEUTIC PAD

(76) Inventor: Levi Emmerik A. Dewaegenaere, s'Gravenwezel (BE)

( * ) Notice: Subject to any disclaimer, the term of this patent is extended or adjusted under 35 U.S.C. 154(b) by 1232 days.

(21) Appl. No.: 13/261,115

(22) PCT Filed: Jul. 1, 2010

(86) PCT No.: PCT/EP2010/059374
§ 371 (c)(1),
(2), (4) Date: Mar. 14, 2012

(87) PCT Pub. No.: WO2011/000917
PCT Pub. Date: Jan. 6, 2011

(65) Prior Publication Data
US 2012/0172956 A1    Jul. 5, 2012

(30) Foreign Application Priority Data

Jul. 3, 2009 (EP) .................................. 09164550
Oct. 13, 2009 (EP) .................................. 09172906

(51) Int. Cl.
*A61F 7/00*    (2006.01)
*A61B 18/00*    (2006.01)

(52) U.S. Cl.
CPC ............ *A61B 18/00* (2013.01); *A61F 7/00* (2013.01); *A61B 2560/0276* (2013.01); *A61F 2007/0054* (2013.01)

(58) Field of Classification Search
USPC ......................................................... 607/104
See application file for complete search history.

(56) References Cited

U.S. PATENT DOCUMENTS 4,114,620 A * 9/1978 Moore ..................... A61F 7/02
                                                    5/421
4,548,212 A    10/1985 Leung
(Continued)

FOREIGN PATENT DOCUMENTS

CN    1399532    2/2003
CN    1460008    12/2003
(Continued)

OTHER PUBLICATIONS

Official Action (English translation) for Chinese Patent Application No. 201080037662.6 dated Aug. 15, 2014, 5 pages.
(Continued)

*Primary Examiner* — Joseph Stoklosa
*Assistant Examiner* — Adam Avigan
(74) *Attorney, Agent, or Firm* — Sheridan Ross P.C.

(57) ABSTRACT

The invention provides for a system for controlling a therapeutic pad having a data storage medium. The system for controlling has means for reading and/or writing the data of the data storage medium of the therapeutic pad, and means for implementing an operational procedure depending on the data of the storage medium of the therapeutic pad. Further, a method for controlling a therapeutic pad having a data storage medium is provided. The method has the steps of reading and/or writing the data of the data storage medium of the therapeutic pad, and implementing operational procedure depending on the data of the storage medium of the therapeutic pad. Furthermore, a computer program product is provided. The computer program product has one or more computer readable media having computer executable instructions for performing the steps of the method as discussed hereinbefore.

15 Claims, 4 Drawing Sheets

(56) References Cited

U.S. PATENT DOCUMENTS

| | | | |
|---|---|---|---|
| 5,662,695 A | 9/1997 | Mason et al. | |
| 5,755,755 A | 5/1998 | Panyard | |
| 5,871,526 A * | 2/1999 | Gibbs | A61F 7/02 165/46 |
| 5,995,868 A | 11/1999 | Dorfmeister et al. | |
| 6,017,337 A | 1/2000 | Pira | |
| 6,086,609 A * | 7/2000 | Buckley | A61F 7/10 607/104 |
| 6,099,521 A | 8/2000 | Shadduck | |
| 6,176,869 B1 | 1/2001 | Mason et al. | 607/104 |
| 6,349,412 B1 | 2/2002 | Dean | |
| 6,508,831 B1 | 1/2003 | Kushnir | |
| 6,763,671 B1 | 7/2004 | Klett et al. | |
| 6,893,453 B2 | 5/2005 | Agarwal et al. | |
| 7,914,563 B2 | 3/2011 | Mason et al. | |
| 7,959,657 B1 * | 6/2011 | Harsy | A61F 7/007 607/104 |
| 2002/0026226 A1 | 2/2002 | Ein | |
| 2002/0096311 A1 | 7/2002 | Kushnir et al. | |
| 2003/0019476 A1 | 1/2003 | Chambers | |
| 2003/0069621 A1 | 4/2003 | Kushnir | |
| 2003/0140928 A1 | 7/2003 | Bui et al. | |
| 2004/0019269 A1 | 1/2004 | Schaefer et al. | |
| 2004/0030373 A1 * | 2/2004 | Ellingboe | A61F 7/02 607/104 |
| 2004/0210273 A1 * | 10/2004 | Wang | A61N 1/37247 607/59 |
| 2005/0091896 A1 * | 5/2005 | Kotik | G06F 19/323 40/633 |
| 2005/0103353 A1 | 5/2005 | Grahn et al. | |
| 2006/0282140 A1 | 12/2006 | Schock et al. | |
| 2007/0055330 A1 * | 3/2007 | Rutherford | A61F 7/007 607/114 |
| 2007/0068651 A1 | 3/2007 | Gammons et al. | |
| 2007/0185553 A1 | 8/2007 | Kennedy | 607/100 |
| 2008/0234788 A1 | 9/2008 | Wasowski | |
| 2009/0018626 A1 | 1/2009 | Levinson et al. | 607/96 |
| 2009/0026471 A1 | 1/2009 | Wu et al. | 257/98 |
| 2009/0118684 A1 | 5/2009 | Da Silva et al. | 604/290 |
| 2009/0131835 A1 | 5/2009 | Voorhees et al. | 600/595 |
| 2009/0326381 A1 | 12/2009 | Yuan et al. | |
| 2010/0069758 A1 | 3/2010 | Barnes et al. | |
| 2010/0081971 A1 | 4/2010 | Allison | |
| 2010/0087900 A1 | 4/2010 | Flint | |
| 2010/0234737 A1 | 9/2010 | Farage | |
| 2011/0046472 A1 | 2/2011 | Schmidt et al. | |
| 2011/0087096 A1 | 4/2011 | Behar | |
| 2012/0101403 A1 | 4/2012 | Dewaegenaere | |
| 2012/0172955 A1 | 7/2012 | Dewaegenaere | |
| 2012/0172957 A1 | 7/2012 | Dawaegenaere | |
| 2012/0179231 A1 | 7/2012 | Dewaegenaere | |

FOREIGN PATENT DOCUMENTS

| | | |
|---|---|---|
| CN | 1541628 | 11/2004 |
| CN | 1741777 | 3/2006 |
| CN | 2933354 | 8/2007 |
| CN | 101132749 | 2/2008 |
| CN | 101261026 | 9/2008 |
| CN | 201129894 | 10/2008 |
| CN | 201135537 | 10/2008 |
| DE | 29716336 | 12/1997 |
| DE | 20019614 | 1/2001 |
| EP | 0033528 | 8/1981 |
| JP | S52-94697 | 8/1977 |
| JP | S64-46454 | 2/1989 |
| JP | 2003-126213 | 5/2003 |
| RU | 2203698 | 5/2003 |
| RU | 2246919 | 2/2005 |
| RU | 50406 | 1/2006 |
| RU | 2373919 | 11/2009 |
| WO | WO 01/62193 | 8/2001 |
| WO | WO 03/000079 | 1/2003 |
| WO | WO 2004/024000 | 3/2004 |
| WO | WO 2007/047247 | 4/2007 |
| WO | WO 2009/026471 | 2/2009 |
| WO | WO 2009/065138 | 5/2009 |

OTHER PUBLICATIONS

Official Action (English translation) for Chinese Patent Application No. 201080037613.2, dated Sep. 2, 2014, 7 pages.
Official Action for U.S. Appl. No. 13/261,116, dated Oct. 3, 2014 25 pages.
Official Action with English Translation for Russia Patent Application No. 2012103552/14, dated Feb. 17, 2015 6 pages.
Decision on Grant with English Translation for Russia Patent Application No. 2012103552/14, dated May 25, 2015 11 pages.
Official Action with English Translation for China Patent Application No. 201080037662.6, dated Feb. 9, 2015 9 pages.
Decision to Grant with English Translation for Russia Patent Application No. 2012103553/14, dated Feb. 24, 2015 8 pages.
Official Action with English Translation for Russia Patent Application No. 2012103545, dated Jan. 26, 2015 6 pages.
Official Action with English Translation for China Patent Application No. 201080037608.1, dated Jun. 3, 2015 14 pages.
Official Action with English Translation for Russia Patent Application No. 2012103543, dated Dec. 8, 2014 9 pages.
Decision on Grant with English Translation for Russia Patent Application No. 2012103543, dated May 29, 2015 14 pages.
Official Action with English Translation for China Patent Application No. 201080037613.2, dated Feb. 17, 2015 14 pages.
Official Action with English Translation for China Patent Application No. 201080037613.2, dated Jul. 31, 2015 14 pages.
Notice of Allowance with English Translation for Russia Patent Application No. 2012103555/14, dated Feb. 12, 2015 5 pages.
Official Action for U.S. Appl. No. 13/261,116, dated Mar. 20, 2015 24 pages.
Official Action for U.S. Appl. No. 13/261,116, dated Jun. 19, 2015 26 pages.
Notice of Allowance for U.S. Appl. No. 13/261,116, dated Aug. 31, 2015 24 pages.
Official Action for U.S. Appl. No. 13/261,118, dated Aug. 28, 2015 9 pages.
Official Action (English translation) for Chinese Patent Application No. 201080037655.6 dated Apr. 18, 2014, 10 pages.
Official Action (English translation) for Chinese Patent Application No. 201080037608.1 dated Apr. 24, 2014, 5 pages.
Official Action for U.S. Appl. No. 13/261,116 dated Mar. 21, 2014, 22 pages.
Official Action for U.S. Appl. No. 13/261,116 dated May 22, 2014, 24 pages.
Official Action (with English translation) for Chinese Patent Application No. 201080037655.6 dated Sep. 25, 2014, 10 pages.
Official Action (with English translation) for Russian Patent Application No. 2012103553/14 dated Oct. 28, 2014, 5 pages.
Official Action (with English translation) for Chinese Patent Application No. 201080037608.1 dated Nov. 15, 2014, 5 pages.
International Search Report and Written Opinion for International (PCT) Patent Application No. PCT/EP10/59372 dated Sep. 24, 2010, 7 pages.
International Preliminary Report on Patentability for International (PCT) Patent Application No. PCT/EP10/59372 dated Jan. 12, 2012, 6 pages.
Official Action (English translation) for Chinese Patent Application No. 201080037655.6 dated Sep. 13, 2013, 9 pages.
Extended European Search Report for European Patent Application No. 09172913.7 dated Apr. 14, 2010, 5 pages.
International Search Report and Written Opinion for International (PCT) Patent Application No. PCT/EP2010/059374 dated Oct. 5, 2010, 10 pages.
International Preliminary Report on Patentability for International (PCT) Patent Application No. PCT/EP2010/059374 dated Jan. 12, 2012, 8 pages.
Official Action (with English translation) for Chinese Patent Application No. 201080037662.6 dated Jan. 3, 2014, 20 pages.

(56) References Cited

OTHER PUBLICATIONS

Extended European Search Report for European Patent Application No. 09172906.1 dated Oct. 5, 2010, 7 pages.
International Search Report and Written Opinion for International (PCT) Patent Application No. PCT/EP2010/059377 dated Sep. 30, 2010, 12 pages.
International Preliminary Report on Patentability for International (PCT) Patent Application No. PCT/EP2010/059377 dated Jan. 12, 2012, 9 pages.
Official Action (English translation) for Chinese Patent Application No. 201080037612.8 dated Oct. 15, 2013, 6 pages.
Extended European Search Report for European Patent Application No. 09172914.5 dated Oct. 6, 2010, 7 pages.
International Search Report and Written Opinion for International (PCT) Patent Application No. PCT/EP2010/059379 dated Sep. 24, 2010, 10 pages.
International Preliminary Report on Patentability for International (PCT) Patent Application No. PCT/EP2010/059379 dated Jan. 12, 2012, 8 pages.
Official Action (with English translation) for Chinese Patent Application No. 201080037608.1 dated Sep. 4, 2013, 19 pages.
Extended European Search Report for European Patent Application No. 09172912.9 dated May 6, 2010, 6 pages.
International Search Report for International Patent Application No. PCT/EP10/59380, dated Jun. 10, 2010, 4 pages.
Written Opinion for International Patent Application No. PCT/EP10/59380, dated Jun. 10, 2010, 4 pages.
International Preliminary Report on Patentability for International Patent Application No. PCT/EP10/59380, dated Jan. 4, 2012, 5 pages.
Official Action (English translation) for Chinese Patent Application No. 201080037613.2, dated Sep. 16, 2013, 7 pages.
Extended European Search Report for European Patent Application No. 09172908.7 dated Oct. 6, 2010, 6 pages.
Official Action for U.S. Appl. No. 13/261,116 dated Nov. 13, 2013, 19 pages.
Official Action for U.S. Appl. No. 13/261,116 dated Feb. 6, 2014, 18 pages.
Decision to Grant for China Patent Application No. 201080037608.1, dated Sep. 29, 2015 2 pages.
Decision to Grant for China Patent Application No. 201080037613.2, dated Jan. 28, 2016 3 pages.
Official Action for U.S. Appl. No. 13/261,114 dated Sep. 18, 2015, 8 pages.
Official Action for U.S. Appl. No. 13/261,114, dated Jan. 14, 2016 15 pages.
Official Action for U.S. Appl. No. 13/261,114, dated Sep. 19, 2016 15 pages.
Official Action for U.S. Appl. No. 13/261,117, dated Oct. 22, 2015 11 pages.
Official Action for U.S. Appl. No. 13/261,117, dated Feb. 10, 2016 16 pages.
Official Action for U.S. Appl. No. 13/261,117, dated Oct. 6, 2016 17 pages.
Official Action for U.S. Appl. No. 13/261,118, dated Dec. 2, 2015 12 pages.
Official Action for U.S. Appl. No. 13/261,118, dated Aug. 25, 2016 10 pages.
Final Action for U.S. Appl. No. 13/261,114, dated Feb. 8, 2017 14 pages.
Official Action for U.S. Appl. No. 13/261,114, dated Jun. 1, 2017 16 pages.
Final Action for U.S. Appl. No. 13/261,114, dated Aug. 24, 2017 16 pages.
Final Action for U.S. Appl. No. 13/261,117, dated Mar. 7, 2017 19 pages.
Official Action for U.S. Appl. No. 13/261,117, dated Jun. 15, 2017 16 pages.
Final Action for U.S. Appl. No. 13/261,118, dated Feb. 9, 2017 12 pages.
Official Action for U.S. Appl. No. 13/261,118, dated May 18, 2017 12 pages.
Final Action for U.S. Appl. No. 13/261,118, dated Aug. 24, 2017 15 pages.
Final Action for U.S. Appl. No. 13/261,117, dated Oct. 19, 2017 18 pages.
Official Action for U.S. Appl. No. 13/261,114, dated Apr. 19, 2018 15 pages.
Official Action for U.S. Appl. No. 13/261,118, dated May 9, 2018 13 pages.
Official Action with English Translation for China Patent Application No. 201080037612.8, dated May 27, 2014 10 pages.
Official Action for U.S. Appl. No. 13/261,116, dated Jul. 21, 2014 22 pages.

* cited by examiner

SYSTEM AND METHOD FOR CONTROLLING THE OPERATION OF A THERAPEUTIC PAD This Patent Application is a US National Phase Patent Application from PCT Application No. PCT/EP2010/059374, filed Jul. 1, 2010 and claiming priority from European Patent Application Nos. 09164550.7, filed Jul. 3, 2009 and 09172906.1, filed Oct. 13, 2009.

The invention relates to a system and method for controlling the operation of a therapeutic pad. In particular, by reading/writing data from/to the pad, its functionality may be adjusted to enhance its medical operation and to thus achieve a quicker healing for a patient.

FIELD OF THE INVENTION

The present invention is in the technical field of therapeutic treatment and diagnosis of a human or animal body.

More particularly, the present invention is in the technical field of therapeutic treatment of a human or animal body by means of a thermal treatment, which ensures the circulation through the pad of a fluid at controlled and actively regulated temperature, pressure and flow. More particularly, the treatment of the body part is carried out through controlled and actively regulated thermal energy exchange between the pad and the body part to which it is applied, such therapeutic pad containing means for associating thermal treatment-related data with the therapeutic pad.

BACKGROUND OF THE INVENTION

Particular ailments or diseases require treatment by the application of cold or heat to a body part, which has a particular beneficial medical outcome, according to the treatment protocol applied (e.g. intensity and duration of treatment). In the past, this was accomplished, for example, by applying ice or cold liquid to the affected area for cryotherapy, and applying a heat source, such as a heated towel, for heat therapy.

It has been discovered that using a thermal pad considerably increases the efficiency and convenience of such treatment.

However, in some cases, merely providing a hot or cold fluid through the pad to heat or cool the body via the fluid flow through the pad is not sufficient: for example, if the body part is swollen (for example, due to an inflammation), the pressure provided by the pad onto the body part may be too strong or too weak if the pad is in use.

Hence, it would be advantageous to allow the specific treatment of the pad to be modified depending on the type of treatment and characteristics of the patient or his illness.

OBJECTS OF THE INVENTION

It is an object of the present invention to provide means enabling a control of the particular treatment for a pad.

It is an object of the present invention to provide a system having means for storing data related to the controlling and for communicating data.

It is a further object of this invention to provide a therapeutic pad with means for allowing patient specific data to be associated with the patient and treatment applied.

It is a further object of this invention to allow treatment related data to be stored and analysed efficiently.

Further objects and advantages of the present invention will be disclosed and become apparent from the following description.

SUMMARY OF THE INVENTION

The present invention relates to a system for controlling a therapeutic pad having a data storage medium. The system comprises means for reading and/or writing the data of the data storage medium of the therapeutic pad, and means for implementing an operational procedure depending on the data of the storage medium of the therapeutic pad. Further, a therapeutic system comprising the above system and a hydraulic device adapted to connect the hydraulic device to the system for controlling a therapeutic pad is provided. More specific features for preferred embodiments are set out in the dependent claims.

More particularly, in a particular embodiment the present invention is an apparatus and system, comprised of A therapeutic pad storing treatment and patient information.

A system responsible for, but not limited to, (i) the active control of the temperature, pressure and flow of a circulating fluid, (ii) the read and write operations on the data stored on the therapeutic pad, (iii) the implementation of the operational procedures defined on the mentioned data, (iv) providing a hardware and software user interface of any kind (e.g. graphical user interface, touch screen, point and click, keyboard) for the input and output of data and instructions by the thermal treatment device operator, (v) the optional printing of labels or reports (hereinafter referred to as 'thermal treatment device').

An optional handheld, portable device or desk device responsible for (i) the read and write operations on the data stored on the therapeutic pad, (ii) the implementation of the operational procedures defined on the mentioned data, (iii) providing a user interface of any kind (e.g. graphical user interface, touch screen, point and click, keyboard) for the input and output of data and instructions by the thermal treatment device operator, (iv) the optional printing of labels or reports.

The operational procedures defined on the mentioned data, which controls the thermal treatment device operation and treatment delivery.

A contactless or contact based communication system between the therapeutic pad and the thermal treatment device A hydraulic connection system to be used for the hydraulic connection of the therapeutic pad and the thermal treatment device, which allows the circulation through the pad of a fluid at controlled and actively regulated temperature, pressure and flow According to the present invention, a system for controlling a therapeutic pad having a data storage medium is provided. Said system for controlling comprises means for reading and/or writing the data of the data storage medium of the therapeutic pad, and means for implementing an operational procedure depending on the data of the storage medium of the therapeutic pad.

In a particular embodiment, the system is adapted to adjust a thermal energy exchange of the therapeutic pad.

In a particular embodiment, the system is a treatment device, more particularly a thermal treatment device.

In a particular embodiment, the system further comprises means for controlling the operational procedure, particularly a temperature sensor, a pressure sensor, and/or a flow sensor.

In a particular embodiment, the system is a portable therapeutic and/or diagnosis device, particularly adapted to be connected to an external printer device.

In a particular embodiment, the system further comprises a data storage unit.

In a particular embodiment, the means for reading and/or writing is a RF reader and/or writer module.

For example, a contactless communication to the pad may be provided using the RFID (radio frequency identification) technology. RFID is a technology similar in theory to bar code identification. With RFID, the electromagnetic or electrostatic coupling in the RF portion of the electromagnetic spectrum is used to transmit signals. An RFID system consists of an antenna and a transceiver, which read the radio frequency and transfer the information to a processing device, and a transponder or tag, which is an integrated circuit containing the RF circuitry and information to be transmitted. High frequency RFID systems (850 MHz to 950 MHz and 2.4 GHz to 2.5 GHz) offer transmission ranges of more than 25 m. In an RFID system, the transponder that contains the data to be transmitted is the "RF tag". An RF reader/writer module (RFID reader/writer module) is a device that is used to interrogate a RFID tag and/or to generate data thereon. The module has an antenna that emits/receives radio waves; the tag responds by sending back its data.

According to the present invention, a therapeutic system is provided. The therapeutic system comprises the system for controlling a therapeutic pad as discussed above, and a hydraulic device having a tube adapted to connect the hydraulic device to the system for controlling a therapeutic pad.

In a particular embodiment, the hydraulic device is adapted to be connected to the therapeutic system via two tubes.

In a particular embodiment, the system for controlling a therapeutic pad comprises two connectors adapted to connect to the two tubes, and the two connectors are embedded in a single plug/socket.

In a particular embodiment, the hydraulic device is adapted to be adjusted by the system for controlling a therapeutic pad.

According to the present invention, a method for controlling a therapeutic pad having a data storage medium is provided. The method comprises the steps of reading and/or writing the data of the data storage medium of the therapeutic pad, and implementing operational procedure depending on the data of the storage medium of the therapeutic pad.

In a particular embodiment, the method further comprises the step of controlling the operational procedure by determining particular parameters.

In one embodiment, a sensor may be provided and may be adapted to determine the body part related parameter(s), such as the skin conductivity, the skin color, the skin temperature, the skin texture, the heart rate, the blood pressure, the blood saturation.

Additionally the system may comprise means for a controlled supply of medication, e.g., a certain pharmaceutical supplied by a drug pump, to the patient, wherein the system determines—via suitable sensors—the patient's response on the medication, namely the change of the body part related parameter(s). The system may provide a certain diagnosis based on the patient's response and/or modify the thermal treatment in a controlled manner in order to optimize the patient's treatment by means of a closed loop (feedback) control.

For example, the combination of treatment by the thermal treatment device in conjunction with other medical treatments, such as, but not limited to antibiotics, anti-inflammatory drugs, and chemotherapy drugs, can cause a positive synergistic treatment effect. In one embodiment, the thermal treatment device may by used to apply cryo-treatment to an area of the body (e.g, the arm) which is infected with a bacteria which is, for example, normally resistant to antibiotics (e.g. methicillin-resistant *Staphylococcus aureus*). The application of cryo-treatment in this way may cause a reduction in bacterial division and/or spread in the tissue, providing more time for the antibiotics to work effectively in the affected area. This may result in a favorable treatment outcome where amputation may have been the only other viable option.

Further, the invention disclosed herein could operate to monitor the patient's progress with regards to cryo-treatment in combination with other medical treatments and update the treatment protocol accordingly, for example, the choice of medicine and optimal dose rate to maximize pharmaceutical efficacy.

The temperature distribution data may be obtained by an IR (infrared) camera and may be displayed to the physician and/or used for feedback control of the thermal treatment. Furthermore, the time lapsed during the thermal treatment may also be taken into account when controlling the thermal treatment based on the determination of the various body part related parameter(s).

While the present invention discusses the use of biofeedback to adapt a treatment protocol, it is advantageous to disclose the optimal means of obtaining a biofeedback reading, which are preferably non-invasive. For example, the amount of thermal exchange between the thermal pad or Peltier thermal exchange element and skin can be determined by using a temperature sensitive surface between such thermal pad or Peltier thermal exchange element and skin. Alternatively, a measurement of power output to the fluid in the thermal pad or the Peltier thermal exchange element itself can provide an indirect determination of thermal exchange with a body. Alternatively, the amount of thermal exchange between a Peltier thermal exchange element and the skin (such Peltier thermal exchange element preferably being constructed in the manned disclosed in U.S. Pat. No. 6,017,337 by Pira) can be determined indirectly by measuring temperature difference between the cold side and hot side of the Peltier element, and the rate of flow of liquid cooling the heat sink on the hot side. Alternatively, a direct measurement of biofeedback (e.g. temperature) from a patient can be obtained by using sensor means to obtain a reading from a drainage catheter, which, for example, has been inserted into the body following knee reconstructive surgery. Although various preferred means of obtaining biofeedback readings have been disclosed herein, other means of obtaining such readings are not excluded.

In a particular embodiment, the controlling step comprises a step of comparing the determined parameters with pre-determined data in a data storage unit.

In a particular embodiment, the controlling step further comprises a step of adjusting the operational procedure depending on the result of the comparing step.

According to the present invention, a computer program product is provided. The computer program product comprises one or more computer readable media having computer executable instructions for performing the steps of the method as discussed above.

In a particular embodiment, the data is a medical protocol information and/or a result of a medical treatment and/or an information relating to the performance and/or lifetime of the pad.

In a particular embodiment, the data of the data storage of the therapeutic pad may be medical data related to the treatment of the pad. As an example, a representation of the information set in the data is listed below. The data as grouped below is not only 'read' data but also 'write' data if labeled accordingly. The information set can be any subset of the following information (but not limited to this information only, as other information of interest can be defined and stored):

Therapeutic Pad Serial Number (S/N)
Pad type (e.g. knee pad, face pad, shoulder pad)
Production batch
Production date
Patient Name (write, only once)
Patient unique identifier (in hospitals or treatment facilities where identifiers are used instead of the patient name) (write, only once)
Protocol Name (name of the protocol used for the treatment of the patient for which the therapeutic pad is used) (write)
Protocol step 1 parameter set (write)
Protocol step 2 parameter set (write)
Protocol identifier (write)
Timestamp of first connection (write only once)
Timestamp last event (write)
Thermal treatment server SN (last thermal treatment server to write on the RF tag) (write)
Type of last event (e.g. disconnection of therapeutic pad, system message, start of treatment) (write)
Treatment output data set (e.g. response of human body to treatment, therapeutic pad performance) (write)

In a particular embodiment, the information to be stored can be part of the following classes, but not limited to: patient information, medical treatment and medical protocol information, intermediate and final treatment results information, diagnosis information, information related to the use, quality, performance and lifetime of the therapeutic pad, traceability information for patients and therapeutic pads.

The primary responsibility of the thermal treatment device is to ensure the circulation through the therapeutic pad of a fluid at controlled and actively regulated temperature, pressure and flow, with the stated ultimate goal to ensure positive outcome for the patient being treated. In order to effectively, efficiently, reliably and safely perform its primary responsibility, the thermal treatment device may require an initial input of information and instruction by an operator (for example, the physician), as well as subsequent inflow of real time information collected through some sensors externally placed, for example, in a treatment device.

DETAILED DESCRIPTION OF THE INVENTION

Figure 1:
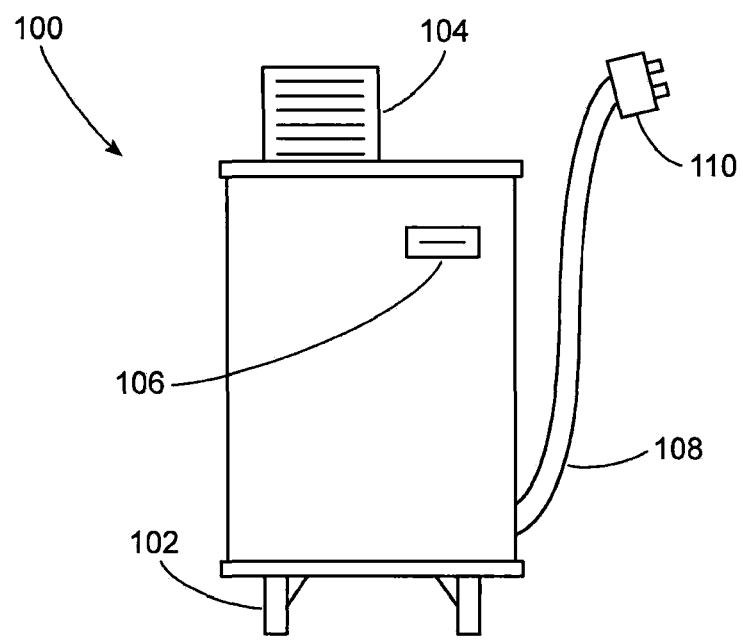
FIG. 1 schematically shows an external device for controlling the therapeutic pad.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. In addition, an aspect described in conjunction with a particular embodiment of the present invention is not necessarily limited to that embodiment and can be practiced in any other embodiments of the present invention.

Figure 6:
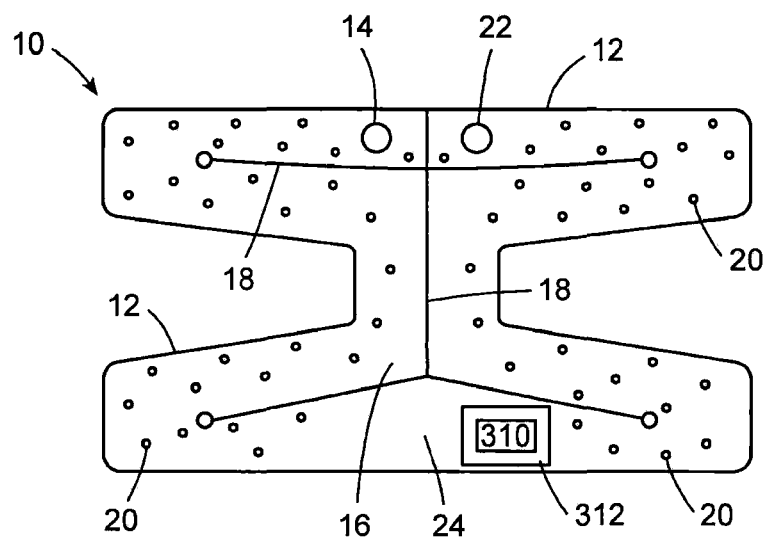
FIG. 6 schematically shows a top view of a therapeutic pad.

Referring now to the invention in more detail, FIG. 1 schematically shows a medical treatment device (100) for controlling a therapeutic pad, for example, the therapeutic pad as schematically shown in FIG. 6. The device may or may not have wheels (102) or other means for facilitating the transportation and handling, so that the device is a portable device. The treatment device (100) is equipped with a hardware and software user interface (104). The user interface (104) may be a touch screen user interface, but any other kind that allows the operator of the treatment device (100) to perform and view the input and request and view the output of data and instructions is possible (included but not limited to hardware keyboard, pointing device, audio input and output). Further, the treatment device (100) can have a printer device, embedded (106) or external (connected through radio or wire to the treatment device (100)), for the printing of labels and reports. Finally, the treatment device (100) may be a thermal treatment device and may be equipped with a hydraulic tube (108) and a hydraulic connector (110) to allow the circulating fluid to reach a therapeutic pad through the hydraulic device (200) described in FIG. 2. The hydraulic connector (110) can be formed by two separate hydraulic connectors or the two connectors can be embedded in a single element, as depicted in FIG. 1.

Figure 2:
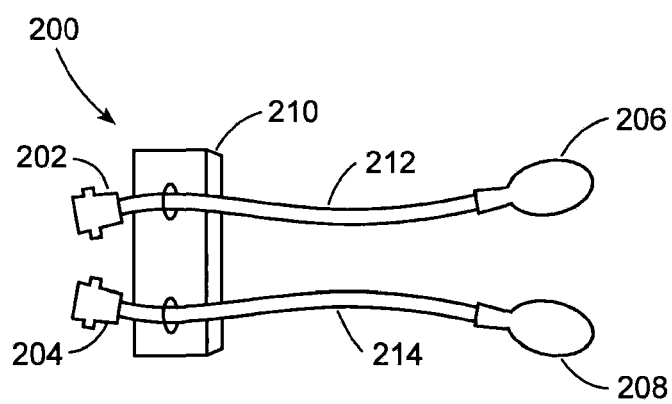
FIG. 2 schematically shows a hydraulic device.

FIG. 2 shows a top view of a hydraulic device (200). The hydraulic device (200) is formed by two tubes (212, 214), two hydraulic connectors connected to the tubes (212, 214), and two hydraulic sealed connections (206, 208). The hydraulic sealed connections are preferably sealed in a non-removable way to the fluid inlet (14) and outlet (22) of the therapeutic pad (10). Preferably the hydraulic device (200) is assembled and forms one single part with the therapeutic pad (10). For example, the hydraulic device and the pad may be integrally formed, e.g. integrally molded. Optionally the hydraulic device (200) can be equipped with an element (210) with the mechanical goal of keeping the tubes close to each other. In an alternative but similar embodiment, the two connectors can be embedded in such an element (210). The hydraulic device (200) allows the circulation of the fluid from a thermal treatment device through the connectors (202, 204) to and through the therapeutic pad (10).

Figure 3:
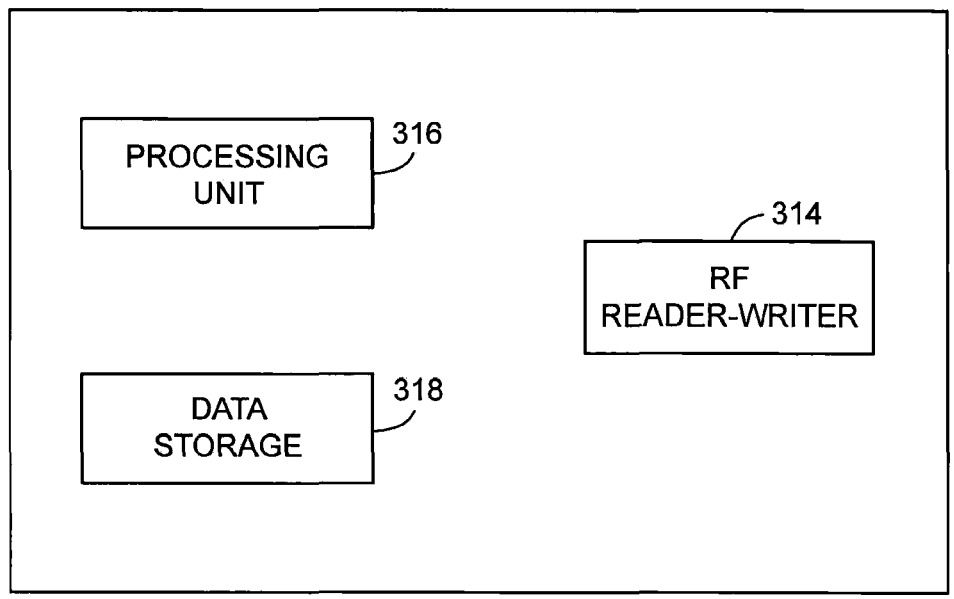
FIG. 3 schematically shows the components of an external system controlling a therapeutic pad.

FIG. 3 shows a functional diagram of the components of an external treatment device, for example, the device (100) as shown in FIG. 1, for controlling the treatment of a pad, for example pad (10) as shown in FIG. 6 as an example, to the body. In a particular embodiment, the processing unit (316), a data storage (318), and a RF reader and/or writer module (314) form a contactless communication system. For example, if a readable and writeable electronic memory chip, e.g. the data storage (310), is placed in a RF tag (312), see also FIG. 4, and attached on or within a part of the pad, the contactless communication system allows a controlling and adjusting of fluid flow, pressure, and/or temperature in the pad.

In a particular embodiment, the treatment and patient information data storage unit is placed on a therapeutic pad (10) or on the hydraulic connection system (device) (200). The preferred embodiment is a contactless communication system, with a readable and writeable electronic memory chip (310) placed in a RF tag (312) placed in the hydraulic connector (202 or 204), but can also be placed in (210), or in a label on the therapeutic pad (10). Any other solution is possible for placing the RF tag. The read and write operations are performed by a RF reader/writer module (314) part of the thermal treatment device (100). The RF reader/writer module (314) is preferably collocated with the processing unit (316). In this case the RF antenna part of the RF reader/writer module (314) can be located for example on the connector (110), and connected to the RF reader/writer module (314) by means of, but not limited to, a coaxial cable. The RE reader/writer module (314) is driven by the processing unit (316), and is either integrated with it or connected to it by means of, for example but not limited to, a SPI bus, a RS232 port. The information is read from and written to a data storage unit (318) by the RF reader/writer module (314). The data storage unit (318) is preferably accessed by the RF reader/writer module (314) through the processing unit (316). An example of a contact based communication system is that of a readable and writeable electronic memory chip placed as described above, but the communication is implemented through an electrical connection (e.g. electric wire and plugs) between the data storage (310) on the therapeutic pad (10) and a reader/writer on the thermal treatment server (100).

Figure 4:
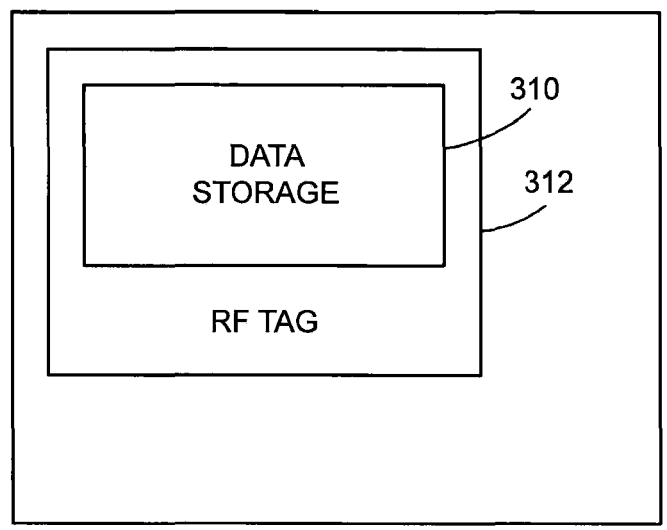
FIG. 4 schematically shows a part of a pad having a RF tag.

FIG. 4 shows a part of the therapeutic pad having an RF tag (312) attached. In this embodiment, the tag 312 comprises a data storage (310) to allow the storage of data received, e.g., from an external device. In a particular embodiment, the storage is a treatment and patient information data storage and is placed on the therapeutic pad (10) via a tag.

In doing so, application of the pad and use of the pad may be efficiently and effectively controlled by the system (treatment device) so that the wearing of the pad is more convenient for the patient and healing is enhanced.

In one embodiment, once the treatment starts, the thermal treatment device will start writing data onto the data storage tag (310). Once the treatment stops, and the user moves to another location, the therapeutic pad (10) will be connected to a new thermal treatment device. The latter will read the information from the data storage tag (310), and by doing so it will be able to implement the right treatment protocol without needing any manual input.

Also, because the thermal treatment device will also log on the data storage tag (310) information related to the therapeutic pad (10) performance, usage, quality, etc., the thermal treatment device will be able to control and regulate the use of expired or non-performing therapeutic pads (10).

Preferably, the therapeutic pad (10) is a disposable unit which is replaced after a pre-determined amount of time, due to treatment protocols, safety, or expiry of the pad. The data storage tag (310) allows the treatment device to disable the pad (10) after a pre-determined amount of time, for example, 10 hours of treatment. At that time, it is anticipated that information from the data storage tag (310) on the therapeutic pad (10) is copied to the replacement therapeutic pad (10), via means of an intermediary device, for example, but not limited to the thermal treatment device.

Additionally or alternatively, information can also be copied onto a storage device held on the patient's person, for example, onto an RF bracelet, for example. For example, such information may be uploaded to a computer network or the Internet, either by the treatment device or from the therapeutic pad (10) preferably using wireless transmission means. Such alternative embodiments advantageously allow data specific to the patient to be collated for various purposes, such as but not limited to, generating or modifying treatment protocols, assessing the current status of the patient on their path to recovery, or collecting data in the process of a clinical trial.

Finally, one of the problems with the kind of therapeutic pad (10) described and the domain of the treatment, is the risk of infections due to improper use of the therapeutic pads (e.g. multiple patient use). The operator is able now to register the patient name, and possibly also to print it and stick it to the therapeutic pad (10). Because the thermal treatment server will ask confirmation of the current patient—therapeutic pad (10) relationship, there will be a further step of control in ensuring the single patient usage of the therapeutic pad (10).

Figure 5:
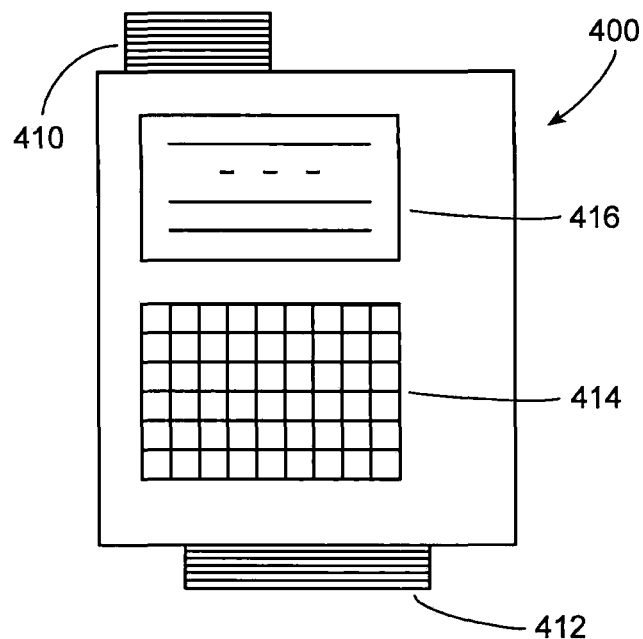
FIG. 5 schematically shows an external handheld device for reading/writing data of a therapeutic pad.

FIG. 5 schematically shows an (optional) handheld device (400), equipped with a hardware and software user interface (414, 416). The user interface (414, 416) depicted in FIG. 6 is a video display (416) with a hardware keyboard (414), but any other kind that allows the operator of the (thermal) treatment device (100) to perform and view the input and to request and view the output of data and instructions is possible (included but not limited to hardware keyboard, pointing device, audio input and output). Further, the handheld device (400) can have a printer device, embedded (412) or external (connected through radio or wire to the handheld device (400)), for the printing of labels and reports. Finally, the handheld device (400) may have a RF reader/writer module (410).

FIG. 6 shows a top view of a therapeutic pad (10) as an example. The shape of the therapeutic pad (10) may be modified to fit to particular part of the body to be treated and depends on the application. The depicted therapeutic pad (10) in FIG. 6 is, for example, for knee application. Other shapes are also possible and may be preferred for different applications.

The therapeutic pad (10) is outlined by externally enclosing welding lines (12). The therapeutic pad receives the fluid, for example, from a thermal treatment device through a fluid inlet (14). The fluid circulates in the therapeutic pad through internal communicating channels (16), delimited by internal welding lines (18) and welding points (20). Finally, the fluid returns to the thermal treatment device through a fluid outlet (22).

Figure 7:
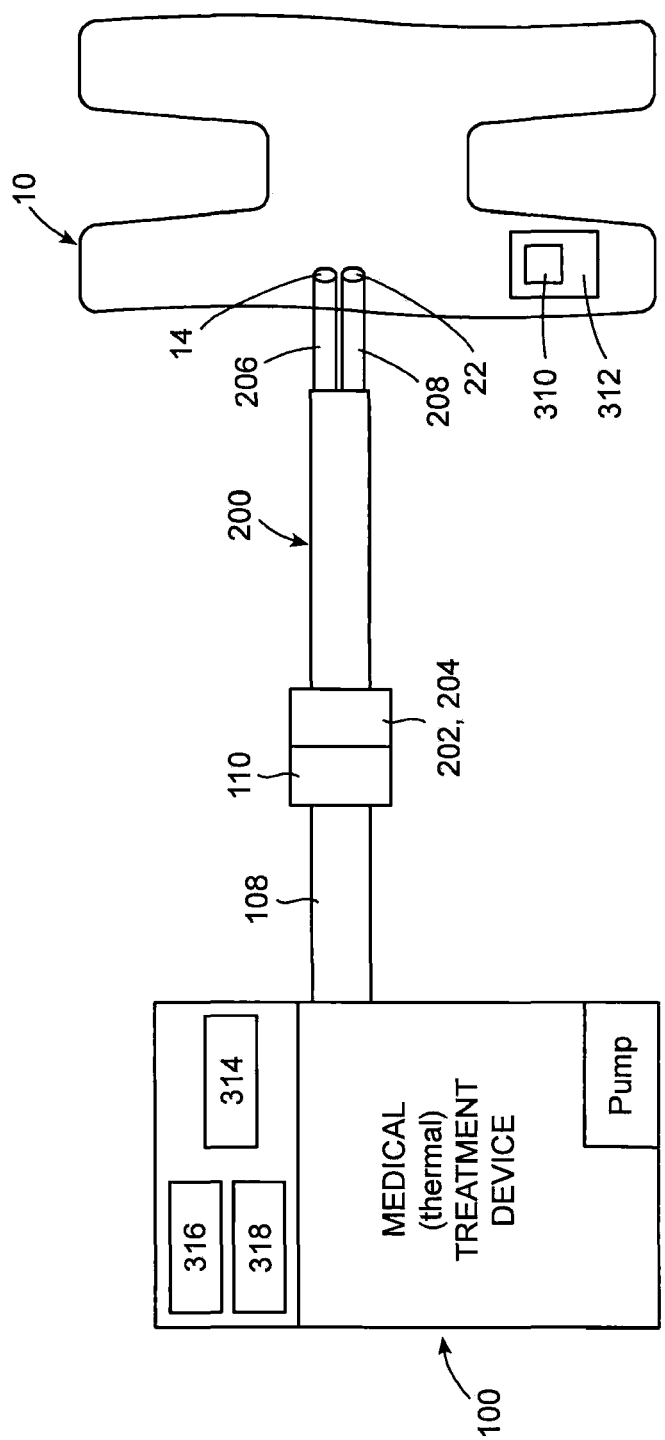
FIG. 7 schematically shows the system controlling the operation of the pad.

FIG. 7 shows the overall system with the arrangement of the medical treatment device (100) and the pad (10) connected to the device (100) via a tube system (108, 110, 202, 204, 206 and 208).

While the invention has been illustrated and described in detail in the foregoing description, such illustration and description are to be considered illustrative or exemplary and non-restrictive; the invention is thus not limited to the disclosed embodiments. Features mentioned in connection with one embodiment described herein may also be advantageous as features of another embodiment described herein without explicitly showing these features. Variations to the disclosed embodiments can be understood and effected by those skilled in the art and practicing the claimed invention, from a study of the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures can not be used to advantage.

The invention claimed is:

1. A system for controlling a therapeutic pad having a data storage medium, comprising
  means for at least one of reading and writing data of the data storage medium of the therapeutic pad, the data storage medium storing a therapeutic pad serial number, a patient identifier and a protocol name, the data storage medium additionally storing a timestamp, a treatment server identifier, an event, and an expiration information, wherein information in the data storage medium of the therapeutic pad allows confirmation of a current patient-therapeutic pad relationship and the data storage medium is an RF tag placed in a hydraulic connector of the therapeutic pad;
  means for implementing an operational procedure depending upon the data of the data storage medium of the therapeutic pad, wherein when the therapeutic pad is attached to a new thermal treatment device, the new thermal treatment device will read data in the data storage medium and will automatically select the operational procedure based at least on the read data from the data storage medium, the therapeutic pad having a shape corresponding to a particular body part to be treated with the operational procedure, the therapeutic pad receiving a fluid, the fluid circulating in the therapeutic pad through internal communication channels, the internal communication channels delimited by internal welding lines and welding points; and
  means for controlling a temperature, a pressure, and flow of the fluid through the therapeutic pad, wherein the system modifies a treatment of the therapeutic pad in a controlled manner through a feedback control to optimize a patient's treatment.

2. The system of claim 1, further comprising means for adjusting a thermal energy exchange of the therapeutic pad.

3. The system of claim 1, further comprising a means for controlling the operational procedure, wherein said means is selected from at least one of a temperature sensor, a pressure sensor, or a flow sensor.

4. The system of claim 1, wherein the system is a portable therapeutic or diagnosis device adapted to be connected to an external printer device.

5. The system of claim 1, further comprising a data storage unit.

6. The system of claim 1, wherein the means for reading or writing is at last one of a RF reader or writer module.

7. The system of claim 1, further comprising
  a hydraulic device having a tube adapted to connect the hydraulic device to the system for controlling a therapeutic pad.

8. The system of claim 7, wherein the hydraulic device is adapted to be connected to the therapeutic system via two tubes.

9. The system of claim 8, wherein the system for controlling the therapeutic pad comprises two connectors adapted to connect to the two tubes, and wherein the two connectors are embedded in a single plug/socket.

10. The system of claim 7, wherein the hydraulic device is adapted to be adjusted by the system for controlling a therapeutic pad.

11. A method to control a therapeutic pad having a data storage medium, comprising the steps of:
  at least one of reading or writing data of the data storage medium to the therapeutic pad, the data storage medium storing a therapeutic pad serial number, a patient identifier and a protocol name, the data storage medium additionally storing a timestamp, a treatment server identifier, and an event, wherein information in the data storage medium of the therapeutic pad allows confirmation of a current patient—therapeutic pad relationship and the data storage medium is a Radio Frequency (RF) tag placed in a hydraulic connector of the therapeutic pad;
  implementing operational procedure depending on the data of the data storage medium of the therapeutic pad, wherein when the therapeutic pad is attached to a new thermal treatment device, the new thermal treatment device will read data in the data storage medium and will automatically select the operational procedure based at least on the read data from the data storage medium, the therapeutic pad having a shape corresponding to a particular body part to be treated with the operational procedure, the therapeutic pad receiving a fluid, the fluid circulating in the therapeutic pad through internal communication channels, the internal communication channels delimited by internal welding lines and welding points; and
  controlling a temperature, a pressure and flow of the fluid through the therapeutic pad, wherein a treatment of the therapeutic pad is modified in a controlled manner through a feedback control in order to optimize a patient's treatment.

12. The method of claim 11, further controlling the operational procedure by determining particular parameters.

13. The method of claim 12, wherein the controlling step includes comparing the determined parameters with predetermined data in a data storage unit.

14. The method of claim 13, wherein the controlling step further comprises
  adjusting the operational procedure depending on the result of the comparing step.

15. A system adapted to control a therapeutic pad having a data storage device, comprising
  a radio frequency identification (RFID) writer/reader that reads and writes data of the data storage device of the therapeutic pad, the data storage device storing a therapeutic pad serial number, a patient identifier and a protocol name, the data storage device additionally storing a timestamp, a treatment server identifier and an event, wherein information in the data storage medium of the therapeutic pad allows confirmation of a current patient—therapeutic pad relationship and the data storage device is a radio frequency (RF) tag placed in a hydraulic connector of the therapeutic pad;
  a processing unit that implements an operational procedure depending upon the data of the data storage medium of the therapeutic pad, wherein when the therapeutic pad is attached to a new thermal treatment device, the new thermal treatment device will read data in the data storage medium and will automatically select the operational procedure based at least on the read data from the data storage device, the therapeutic pad having a shape corresponding to a particular body part to be treated with the operational procedure, the therapeutic pad receiving a fluid, the fluid circulating in the therapeutic pad through internal communication channels, the internal communication channels delimited by internal welding lines and welding points; and
one or more sensors that control a temperature, a pressure and flow of the fluid through the therapeutic pad, wherein the system modifies a treatment of the therapeutic pad in a controlled manner through feedback control to optimize a patient's treatment.

* * * * *